United States Patent [19]

Schuppan et al.

[11] 4,051,247

[45] Sept. 27, 1977

[54] METHOD OF USING 7-HYDROXY-BENZO[IJ]QUINOLIZINE-2-CARBOXYLIC ACID DERIVATIVES

[75] Inventors: Dietrich Schuppan, St. Paul; John F. Gerster; Charles M. Leir, both of Woodbury, all of Minn.

[73] Assignee: Riker Laboratories, Inc., Northridge, Calif.

[21] Appl. No.: 669,845

[22] Filed: Mar. 24, 1976

Related U.S. Application Data

[62] Division of Ser. No. 567,510, April 14, 1975, Pat. No. 3,985,753.

[51] Int. Cl.² .............................................. A61K 31/47
[52] U.S. Cl. .................................................... 424/258

[58] Field of Search ..................... 260/287 P; 424/258

[56] References Cited

U.S. PATENT DOCUMENTS

| 3,917,608 | 11/1975 | Ellis et al. | 424/258 |
| 3,924,042 | 12/1975 | Gerster | 424/258 |

*Primary Examiner*—Donald G. Daus
*Assistant Examiner*—David E. Wheeler
*Attorney, Agent, or Firm*—Cruzan Alexander; Donald M. Sell; Carolyn A. Bates

[57] ABSTRACT

Certain substituted 6,7-dihydro-7-hydroxy-1-oxo-1H,5H-benzo[ij]quinolizine-2-carboxylic acids and salt and ester derivatives thereof are described. These compounds are useful antibacterial agents.

2 Claims, 2 Drawing Figures

METHOD OF USING 7-HYDROXY-BENZO[IJ]QUINOLIZINE-2-CARBOXYLIC ACID DERIVATIVES

This is a division of application Ser. No. 567,510, filed Apr. 14, 1975, now U.S. Pat. No. 3,985,753.

BACKGROUND OF THE INVENTION

This invention relates to derivatives of the heterocyclic system known as benzo[ij]quinolizine. A further aspect of the invention relates to the use of the compounds as antimicrobial agents. Pharmaceutical compositions containing the compounds are also included within the scope of the invention.

1. Description of the Prior Art

The compound 6,7-dihydro-1-oxo-1H,5H-benzo[ij]-quinolizine-2-carboxylic acid and various derivatives thereof, including ester and salt derivatives, are disclosed in U.S. Patent Application Ser. No. 303,254 filed Nov. 2, 1972, as having antimicrobial activity. That disclosure includes other compounds having similar activity in which the benzo ring portion of the molecule is substituted by a variety of substituents in the 8, 9 and 10 positions, and the alicyclic ring is substituted by methyl, ethyl, or trifluoromethyl groups. These compounds do not contain any functional substituents on the alicyclic ring.

2. Description of the Invention

This invention relates to certain 6,7-dihydro-7-hydroxy-1-oxo-1H,5H-benzo[ij]quinolizine-2-carboxylic acids and ester and salt derivatives thereof. These compounds having utility as antimicrobial agents. The structure and numbering system of the heterocyclic system of these compounds are

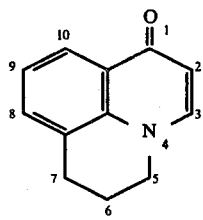

Compounds of the invention are defined by the formula

Formula 1

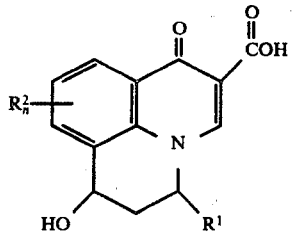

wherein $R^1$ is hydrogen, methyl, or ethyl; $R^2$ is methyl, ethyl, methoxy, halogen, hydroxy, nitro, amino, acetamido or formamido; $n$ is zero, one or two, and when $n$ is 2, $R^2$ may be methylenedioxy

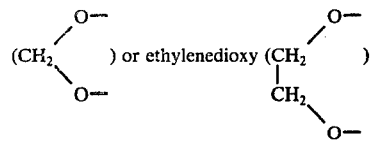

bonded to adjacent carbon atoms; and when $R^2$ is ethyl, methoxy, nitro, amino, acetamido or formamido, and $n$ is 2, each $R^2$ must be different; and lower alkyl esters and pharmaceutically acceptable salt derivatives of said acids.

The terms "lower alkyl", "alkyl" or the abbreviation "alk" as used herein refers to straight and branched-chain alkyl groups having 1 to 4 carbon atoms.

It is well known in the art that pharmaceutically acceptable salts such as alkali metal, alkaline earth, aluminum, iron, and other metal and amine salts can be readily formed from biologically active acids. These salts are essentially equivalent to the acids with respect to biological activity, and in some respects may even offer advantages over the acids in absorption, formulation and the like due to their increased water solubility.

Salts of the free acid compounds of the invention are prepared by reacting the corresponding acid with a base and evaporating to dryness. Inorganic bases or organic bases such as sodium methoxide or an amine may be used. Presently preferred salts are alkali metal and alkaline earth salts.

The free acid compounds of the invention are preferred in that they exhibit the highest levels of antimicrobial activity.

The lower alkyl esters and salts of the acid compounds are useful as intermediates for the preparation of the corresponding acids, and in many cases these esters and salts are also useful as antimicrobial agents. The preferred esters are ethyl esters.

Compounds of formula 1 wherein $R^1$ is methyl or ethyl represent a preferred subclass of antimicrobial agents. Also preferred are compounds wherein $n$ is one and $R^2$ is halogen, methyl, methoxy or hydroxy. When $R^2$ is halogen, it is preferably fluorine, chlorine or bromine. Another preferred subclass of compounds is that wherein $n$ is two and $R^2$ is methylenedioxy or ethylenedioxy bonded to adjacent carbon atoms.

Compounds of formula 1 wherein $R^2$ is nitro or amino are particularly useful as intermediates for the preparation of other compounds of the invention.

All compounds of formula 1 will have at least one optically active center at the 7-position. Compounds wherein $R^1$ is methyl or ethyl have an additional optically active center. Thus, compounds of the invention may have up to four or more optical isomers. Pure optical isomers of the compounds may be synthesized, but the process is tedious and economically impractical using presently available techniques. Although it has been found that in some cases, one isomer may have more antimicrobial activity than another, sufficient activity is obtained with a compound containing a mixture of isomers so as to make isolation of the individual isomers unnecessary. Since the acid compounds of the invention have a reactive hydroxyl group in the 7-position and a reactive acid group, they have potential utility as monomers for making certain polyesters.

The antimicrobial activity of the compounds of the invention can be demonstrated by the known, standard plate dilution method for bacterial susceptibility to antibiotics. (See English Antibiot. Chemother, Vol. 1, 118, 1951.) The culture medium employed permits susceptibility testing of fastidious microorganisms toward antibiotics, sulfonamides, and other chemotherapeutic agents. Tryptone soy agar (oxoid) of the following composition is the culture medium.

| Oxoid tryptone | 15 g |
| --- | --- |
| Oxoid soy peptone | 5 g |
| Sodium chloride | 5 g |
| Oxoid agar-agar No. 3 | 15 g |
| Water | 1 liter |

Using this test, the compounds of the invention have been found to have a broad spectrum of activity against gram-positive and gram-negative microorganisms.

The compounds of the invention are active against microorganisms either in the absence or presence of ten percent horse serum.

In the test procedure the amount of a compound required to give complete, partial, or no inhibition of microbial growth on the agar plates is determined. The compound selected for evaluation is added to the agar medium to give concentrations of one, ten and one hundred milligrams per liter. A series of plates is prepared with these concentrations, and each series includes control plates containing only agar. Ten percent horse serum is added to one series of such plates. Aliquots of broth culture of each of eleven species of microorganisms are innoculated onto the plates. The plates are incubated at 37° C in a ten percent carbon dioxide atmosphere for 18 to 24 hours. The microbial growth on each plate is read visually, and minimal inhibitory concentrations are recorded.

The microorganisms for this test were:
1. *Stapylococcus aureus*
2. *Bacillus subtilus*
3. *Pseudomonas aeruginosa*
4. *Escherichia coli*
5. *Streptococcus sp.* *
6. *Aspergillus niger*
7. *Candida albicans*
8. *Mima polymorpha*
9. *Herellea vaginicola*
10. *Klebsiella pneumoniae*
11. *Streptococcus fecaelis*

*Strains isolated from dental caries in rats or hamsters at the National Institute of Dental Health and grown in PFY or APT agar.

Some of the compounds of the invention have also shown activity toward anaerobic bacteria, e.g., Bacteroides sp. and *Clostridium welchii.*

It will be understood by those skilled in the art that the species used are representative indicator species, as it would be impractical to screen against all bacteria. It is well known in the art that broad spectrum activity can be predicted on the basis of activity shown against selected representative bacterial species.

The compounds of the invention are active against microorganisms in vitro or topically. In vitro activity is useful in itself since antimicrobial agents may be used as components of disinfecting solutions for disinfecting items such as medical and dental equipment. The preferred compounds of the invention are also active in vivo in animals.

Many of the compounds of the invention are active when administered orally to animals. They are excreted in the urine, and are useful in treating urinary tract bacterial infections in mammals. An advantage of the compounds is that they appear to be conjugated to a minimal degree by the mammalian organism. Because the compounds are not significantly inactivated by normal metabolic processes, higher levels of the active forms of the compounds can be maintained in the blood and urine.

The acute oral toxicity of the preferred compounds of the invention is generally moderate to low compared with the effective oral dose, and they have a fair to excellent therapeutic ratio.

Presently preferred compounds of the invention have a broad spectrum of antimicrobial activity and a good therapeutic ratio ($LD_{50}/ED_{50}$).

These compounds are:
9-chloro-6,7-dihydro-7-hydroxy-1-oxo-1H,5H-benzo[ij]quinolizine-2-carboxylic acid;
6,7-dihydro-9-fluoro-7-hydroxy-5-methyl-1-oxo-1H,5H-benzo[ij]-quinolizine-2-carboxylic acid;
9-chloro-6,7-dihydro-7-hydroxy-5-methyl-1-oxo-1H,5H-benzo[ij]quinolizine-2-carboxylic acid;
6,7-dihydro-7-hydroxy-5-methyl-1-oxo-1H,5H-benzo[ij]quinolizine-2-carboxylic acid;
6,7-dihydro-5,9-dimethyl-7-hydroxy-1-oxo-1H,5H-benzo[ij]quinolizine carboxylic acid;
6,7-dihydro-9-methoxy-5-methyl-7-hydroxy-1-oxo-1H,5H-benzo[ij]quinolizine-carboxylic acid; and
6,7-dihydro-5,8-dimethyl-7-hydroxy-1-oxo-1H,5H-benzo[ij]quinolizine-2-carboxylic acid.

The acidic compounds of the invention are ordinarily white or yellowish to brown crystalline or amorphous materials when purified. They are substantially insoluble in water, lower alcohols or hydrocarbons and are more soluble in halogenated solvents and dimethylformamide and the like. The esters are generally somewhat more soluble in organic solvents. The alkali metal salts have appreciable solubility in water and lower alcohols.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable. The formulation is used by immersing objects to be treated therein, or by local application to an infected area.

The amount of compound to be used, for example, in the treatment of a microbial urinary infection by oral administration, will be an effective amount less than a toxic amount. The amount to be administered to control an infection will depend upon the species, sex, weight and physical condition of the patient as well as other variable factors. This judgment is well within the skill of the medical practitioner. Usually the amount will be less than 100 mg/kg per dose. Conveniently this dose is administered in the form of conventional pharmaceutical preparations such as capsules, tablets, emulsions, solutions and the like. Excipients, fillers, coatings, etc. are employed with tablets or capsules, as is well known in the art.

Compounds of the invention are required to contain the functional and reactive hydroxy group in the 7-position of the heterocyclic system. These 7-hydroxy compounds must be prepared from the corresponding novel 7-oxo compounds which are prepared from known starting materials through an extended and complex synthetic sequence. Several novel types of intermediates are formed during this sequence.

DESCRIPTION OF THE DRAWINGS

Understanding of the synthesis of compounds of the invention will be facilitated by reference to the accompanying drawings wherein sequence A.

In Step 1 of sequence A, an aniline, substituted by the appropriate $R^2$ group or groups, is condensed with a dialkyl alkoxymethylenemalonate such as diethyl ethoxymethylenemalonate by heating at 120° to 150° C. The intermediate formed is condensed by heating at a temperature of 150° to 300° C. in a high boiling inert solvent such as diphenyl ether or mixtures of diphenyl ether and biphenyl (e.g. Dowtherm A) to give the ethyl 4-hydroxyquinoline-3-carboxylate product of step 1.

Step 2 of sequence A is the saponification of the ester product of Step 1. This step is successfully carried out using, e.g., aqueous alkali metal hydroxides such as sodium or potassium hydroxide.

The free acid product of step 2 is decarboxylated in step 3 of sequence A, e.g. by heating in an inert high boiling solvent such as diphenyl ether. The product formed is a substituted 4-hydroxyquinoline.

Step 4 of sequence A is the reaction of phosphorous oxychloride with the 4-hydroxyquinoline product of step 3 in an inert solvent to give replacement of the hydroxy group by chlorine. In step 5 of sequence A, the 4-chloro substituent is replaced by an alkoxy group such as methoxy by reaction with methanolic sodium methoxide to provide the substituted 4-methoxyquinoline intermediate. The hydroxy group is thereby blocked and protected from reaction with the alkyl lithium during the next step of the reaction.

In step 6 of sequence A, the 4-methoxyquinoline intermediate is reacted with methyl or ethyl lithium to give a methyl or ethyl substitution in the 2-position. This reaction is carried out carefully under dry conditions in an inert solvent such as diethyl ether or tetrahydrofuran, generally at temperatures of −30° to 0° C. In the second part of this step the alkoxy group is converted back to hydroxy by acidic hydrolytic cleavage. The product is shown as its tautomeric form, a novel substituted 2-alkyl-4-oxo-1,2,3,4-tetrahydroquinoline.

Figure 1:
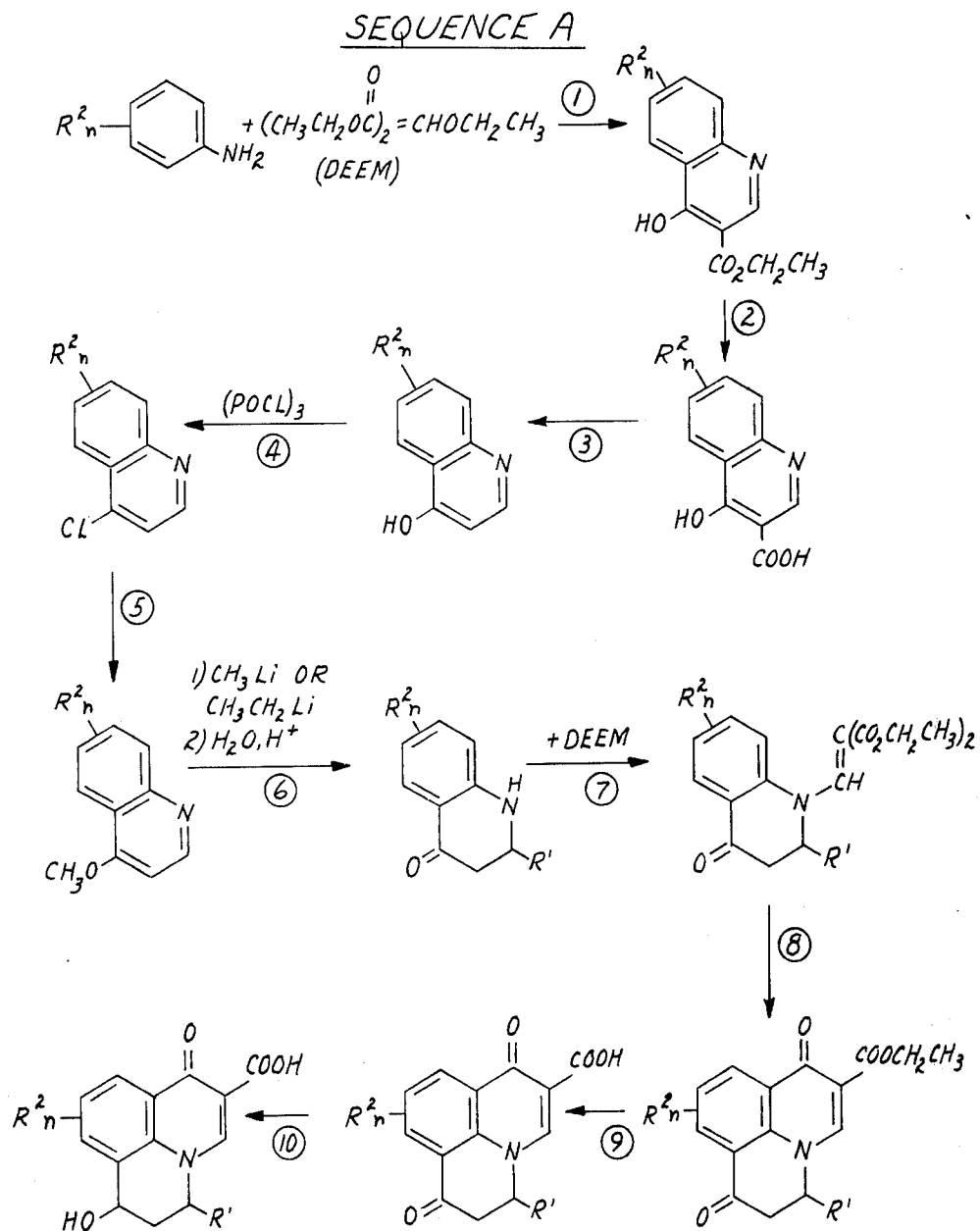
FIG. 1, shows the preparation of compounds of the invention wherein $R^1$ is methyl or ethyl, and sequence B shows the preparation of compounds wherein $R^1$ is hydrogen.
Figure 2:
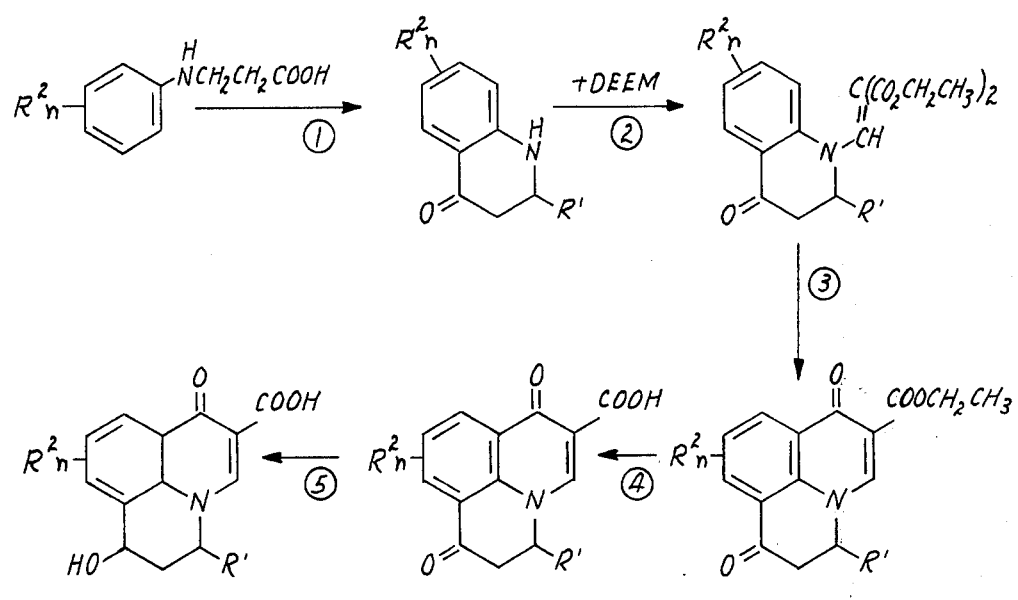

Step 1 of sequence B, FIG. 2, is a known cyclization reaction described for example, in the Journal of Organic Chemistry 28, 1134 (1963), and comprises reacting a 2anilinopropionic acid with polyphosphoric acid at a temperature of 110° to 130° C. This reaction provides known intermediates which are 4-oxo-1,2,3,4-tetrahydroquinolines and $R^1$ is hydrogen. Steps 2-5 of sequence B are identical to steps 8-11, respectively of sequence A.

In step 7 of sequence A (step 2 of sequence B), the 4-oxo-1,2,3,4-tetrahydroquinoline intermediate is heated with a dialkyl alkoxymethylenemalonate such as diethyl ethoxymethylenemalonate at 130° to 200° C. to effect a condensation and provide a novel N-substituted tetrahydroquinoline intermediate. This intermediate is condensed in step 8 (step 3 of sequence B) by heating in the presence of polyphosphoric acid at 100° to 140° C to provide a novel alkyl 6,7-dihydro-1,7-dioxo-1H,5H-benzo[ij]quinolizine-2-carboxylate intermediate.

The ester intermediate obtained in step 8 is saponified in step 9 (step 4 of sequence B) using, for example, an aqueous alkali metal hydroxide such as sodium or potassium hydroxide, to provide the novel intermediate acid.

The 7-oxo group is reduced in step 10 (step 5 of sequence B) using a selective metal hydride reducing agent, preferably sodium borohydride.

The compounds of formula I wherein $R^2$ is nitro are readily prepared by nitration of other compounds of formula I. These nitro compounds may be reduced using e.g., iron and hydrochloric acid, hydrogen and Raney nickel or platinum on charcoal to prepare compounds wherein $R^2$ is amino. Compounds of formula I wherein $R^2$ is amino react with acetic anhydride or formic acid to provide compounds wherein $R^2$ is acetamido or formamido, respectively.

Compounds of formula I wherein $R^2$ is methoxy are reacted in hydrobromic acid to provide compounds wherein $R^2$ is hydroxy. One class of novel intermediates formed during the process of synthesizing the final products of the invention is represented by the formula

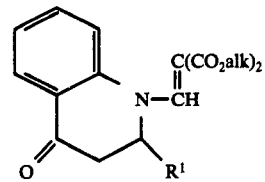

Formula II wherein *alk* is an alkyl radical having 1 to 4 carbon atoms.

A second class of novel intermediates of the invention may be represented by the formula

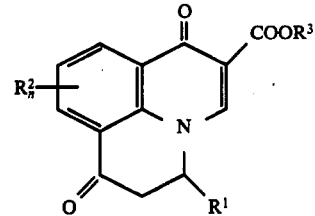

Formula III wherein $R^3$ is hydrogen or lower alkyl.

The following non-limiting examples are provided to illustrate the compounds of the invention and the synthetic methods used to obtain them.

EXAMPLE 1 - STEP 1

A mixture of 66.6 g (0.6 mole) of 4-fluoroaniline and 129.79 g (0.6 mole) of diethyl ethoxymethylenemalonate was prepared under a nitrogen atmosphere and heated to 140° C. The ethanol generated was allowed to vaporize during a reaction time of about one hour. To the mixture was added 500 ml of diphenyl ether. The mixture was stirred and heated to its reflux temperature, and maintained at reflux for 15 minutes. The mixture was then cooled, and diethyl ether was added. The product was separated by filtration, washed with diethyl ether and air dried to provide 97.3 g (69% yield) of ethyl 6-fluoro-4-hydroxyquinoline-3-carboxylate.

EXAMPLE 2 - STEP 2 AND 3

A mixture of 94 g (0.4 mole) of ethyl 6-fluoro-4-hydroxyquinoline-3-carboxylate from example 1, 80 g (2.0 mole) of sodium hydroxide and 200 ml of water was heated to its reflux temperature and held at that temperature while stirring for 30 minutes. The hot solution was poured into a mixture of ice and hydrochloric acid. The acid solution was filtered, washed with water and suctioned dry. The solid obtained was dissolved in 200 ml of diphenyl ether, and the solution heated to its reflux temperature and maintained at reflux for less than 5 minutes. After cooling for several hours the solid precipitate was separated and washed with diethyl ether. The identity of the product, 6-fluoro-4-hydroxyquinoline, was confirmed by infrared and nuclear magnetic resonance spectral analyses.

EXAMPLE 3 - STEP 4 AND 5

To a stirred solution of 62.5 g (0.383 mole) of 6-fluoro-4-hydroxyquinoline from example 2 in 200 ml. of 1,2-dichloroethane was added in small portions 88 g (0.575 mole) of phosphorous oxychloride while maintaining the temperature at 30° to 40° C. The mixture was heated to its reflux temperature and maintained at reflux for 90 minutes.

The mixture was cooled, slurried in 500 ml of diethyl ether and filtered, and the residue was washed with diethyl ether. The organic filtrate was extracted twice with water. The residue was added to the aqueous extracts and the mixture was made basic and filtered. The residue was dissolved in chloroform. The chloroform solution was dried, filtered and evaporated in vacuo. The residue was slurried into hexane and then filtered to provide 58 g (86% yield) of 4-chloro-6-fluoroquinoline.

This intermediate was added to 0.4 mole of methanolic sodium methoxide. The mixture was heated to its reflux temperature and refluxed under a nitrogen atmosphere for about 16 hours. The solution was cooled, filtered, and evaporated in vacuo. The residue was slurried with water and extracted into diethyl ether. The ether extracts were dried and evaporated in vacuo to give 53.1 g (94% yield) of 6-fluoro-4-methoxyquinoline.

EXAMPLE 4 - STEP 6

A stirred solution of 25.8 g (0.146 mole) of 6-fluoro-4-methoxyquinoline from example 3 in 300 ml of tetrahydrofuran was heated under a nitrogen atmosphere to its reflux temperature and then cooled to −20° C. To the cold solution was added 90 ml of 1.82 M methyl lithium in diethyl ether over a period of 0.5 hour. After adding 40 ml of the solution, the reaction temperature was allowed to rise to 0° C. After the addition of methyl lithium was completed, the reaction temperature was allowed to rise to 15° C. The solution was then poured into 1200 ml of a mixture of ice water and hydrochloric acid. After stirring for 0.5 hour the mixture was extracted with about 1200 ml of diethyl ether. The organic layer was dried, filtered and evaporated in vacuo to provide a yellow solid. The product was recrystallized from carbon tetrachloride to give 9.5 g (37% yield) of 6-fluoro-2-methyl-4-oxo-1,2,3,4-tetrahydroquinoline.

EXAMPLE 5 - STEP 7 AND 8

A stirred mixture of 12 g (0.067 mole) of 6-fluoro-2-methyl-4-oxo-1,2,3,4-tetrahydroquinoline from example 4 and 14.8 g (0.070 mole) of diethyl ethoxymethylenemalonate was heated gradually to 160° to 180° C. while removing the ethanol generated by distillation. After 0.5 hour the mixture was cooled to 60° C., and 30 g of polyphosphoric acid was added. This mixture was heated gradually to 150° to 160° C. and maintained at 155° to 160° C. for 5 to 10 minutes. Following cooling, water was added, and the mixture was kneaded to produce an orange powder which was separated by filtration. Recrystallization from a mixture of 500 ml of 95% ethanol and 100 ml of glacial acetic acid gave a yellow product, ethyl 6,7-dihydro-1,7-dioxo-9-fluoro-5-methyl-1H,5H-benzo[ij]quinolizine-2-carboxylate, m.p. 262°–265° C.

EXAMPLE 6 - STEP 9

To a refluxing solution of 5.8 g (0.0191 mole) of ethyl 6,7-dihydro-1,7-dioxo-9-fluoro-5-methyl-1H,5H-benzo[ij]quinolizine-2-carboxylate from example 5 in 50 ml of acetic acid was added 50 ml of 6N hydrochloric acid. After heating at reflux for one hour, the mixture was cooled, 100 ml of water added and the product separated by filtration. The yellow solid was 6,7-dihydro-1,7-dioxo-9-fluoro-5-methyl-1H,5H-benzo[ij]quinolizine-2-carboxylic acid. Analysis:

Calculated for $C_{14}H_{10}FNO_4$: %C, 61.1; %H, 3.7; %N, 5.1. Found: %C, 61.0; %H, 3.5; %N, 5.1.

EXAMPLE 7 - STEP 10

A solution of 2.8 g (0.01 mole) of 9-chloro-6,7-dihydro-1,7-dioxo-1H,5H-benzo[ij]quinolizine-2-carboxylic acid from example 6 in 100 ml of water was prepared by suspending the acid in water, adding excess dilute sodium hydroxide and warming. To this solution waas added 0.15 g (0.04 mole) of sodium borohydride, and the mixture was stirred at room temperature for 6 hours. The mixture was then acidified with dilute hydrochloric acid and the solid product separated by filtration. The product was washed successively with water, methanol and diethyl ether. The solid was recrystallized from an acetic acid-N,N-dimethylformamide mixture to provide 1.6 g of a tan solid which was 9-chloro-6,7-dihydro-7-hydroxy-1-oxo-1H,5H-benzo[ij]quinolizine-2-carboxylic acid, m.p. >250° C. (yield 57%). Analysis:

Calculated for $C_{13}H_{10}ClNO_4$: %C, 55.8; %H, 3.6; %N, 5.0; Found: %C, 55.6; %H, 3.7; %N, 5.0.

The following examples illustrate other compounds of the invention which were prepared using the method of examples 1 to 7.

EXAMPLE 8

6,7-dihydro-9-fluoro-7-hydroxy-5-methyl-1-oxo-1H,5H-benzo[ij]quinolizine-2-carboxylic acid. Analysis:

Calculated for $C_{14}H12FNO_4$: %C, 60.7; %H, 4.4; %N, 5.1, Found: %C, 60.7; %H, 4.2; %N, 5.0.

EXAMPLE 9

9-chloro-6,7-dihydro-7-hydroxy-5-methyl-1-oxo-1H,5H-benzo[ij]quinolizine-2-carboxylic acid, m.p. >250° C.

Analysis: Calculated for $C_{14}H_{12}ClNO_4$: %C, 57.2; %H, 41.1; %N, 4.8; Found: %C. 56.8; %N, 4.1; %H, 4.8.

EXAMPLE 10

6,7-dihydro-7-hydroxy-5-methyl-1oxo-1H,5H-benzo[ij]quinolizine-2-carboxylic acid, m.p. >250° C.

Analysis: Calculated for $C_{14}H_{13}NO_{21}$: %C, 64.9; %H, 5.1; %N, 5.4; Found: %C, 64.3; %H, 5.0; %N-5.2.

EXAMPLE 11

6,7-dihydro-5,9-dimethyl-7-hydroxy-1-oxo-1H,5H-benzo[ij]quinolizine-2-carboxylic acid, m.p. >260° C.

Analysis: Calculated for $C_{15}H_{15}NO_4$: %C, 65.9; %H, 5.5; %N, 5.1; Found: %C, 65.3; %H, 5.5; %N 4.9.

EXAMPLE 12

6,7-dihydro-9-methoxy-5-methyl-7-hydroxy-1-oxo-1H,5H-benzo-[ij]quinolizine-carboxylic acid, m.p. >260° C.

Analysis: Calculated for $C_{15}H_{15}NO_5$: %C, 62.3; %H, 5.2; %N, 4.8; Found: %C, 61.8; %H, 5.1; %N, 4.8.

EXAMPLE 13

6,7-dihydro-5,8-dimethyl-7-hydroxy-1-oxo-1H,5H-benzo[ij]quinolizine-2carboxylic acid, m.p. >260° C.

Calculated for $C_{15}H_{15}NO_4$: %C, 65.9; %H, 5.5; %N, 5.1; Found: %C, 65.6; %H, 5.4; %N, 4.9.

The following table I illustrates compounds of formula I which may be prepared from the starting materials shown by following the reduction step of Example 7. The novel starting materials are prepared according to the synthetic method described in examples 1-6.

Table 1

| Example No. | Starting Material | Product |
|---|---|---|
| 14 | (structure) | (structure) |
| 15 | (structure) | (structure) |
| 16 | (structure) | (structure) |
| 17 | (structure) | (structure) |
| 18 | (structure) | (structure) |
| 19 | (structure) | (structure) |

Table 1-continued

| Example No. | Starting Material | Product |
|---|---|---|
| 20 | [structure: 6-Br, 8-(COCH2CH(CH3)-) quinolizine with COOH] | [structure: same with CHOH instead of CO] |
| 21 | [structure: 5,6-diCl, 8-(COCH2CH(CH3)-) quinolizine with COOH] | [structure: same with CHOH instead of CO] |
| 22 | [structure: 6-Cl, 7-NH2, 8-(COCH2CH(CH3)-) quinolizine with COOH] | [structure: same with CHOH instead of CO] |

EXAMPLE 23

This example illustrates the preparation of compounds of formula 1 wherein $R^2$ is nitro.

A solution of 0.1 mole of 6,7-dihydro-7-hydroxy-5-methyl-1-oxo-1H,5H-benzo[ij]quinolizine-2-carboxylic acid in 150 ml. of concentrated sulfuric acid is treated with a mixture of 150 ml. of concentrated sulfuric acid and 10 ml. of nitric acid while keeping the temperature below 30° C. The solution is stirred for about 24 hours, poured over ice and partially neutralized to a pH of 2 with ammonium hydroxide. The product, 6,7-dihydro-7-hydroxy-5-methyl-10-nitro-1-oxo-1H,5H-benzo[ij]-quinolizine-2-carboxylic acid is isolated by filtration.

EXAMPLE 24

This example illustrates the preparation of compounds of formula I wherein $R^2$ is amino.

6,7-dihydro-7-hydroxy-5-methyl-10-nitro-1-oxo-1H,5H-benzo[ij]quinolizine-2carboxylic acid (0.05 mole) is dissolved in 400 ml. of aqueous potassium hydroxide and hydrogenated on a Parr apparatus at an initial hydrogen pressure of 50 psi using Raney nickel catalyst. The mixture is filtered, and the filtrate is adjusted to a pH of 6 with hydrochloric acid. The product, 10-amino-6,7-dihydro-7-hydroxy-5-methyl-1-oxo-1H,5H-benzo[ij]quinolizine-2-carboxylic acid, is separated by filtration.

EXAMPLE 25

This example illustrates the preparation of compounds of formula I wherein $R^2$ is hydroxy and $n$ is two.

Starting with 3,5-dimethoxyaniline and following the method of examples 1 to 7, one obtains 6,7-dihydro-8,10-dimethoxy-7-hydroxy-5-methyl-1-oxo-1H,5H-benzo[ij]quinolizine-2-carboxylic acid. This intermediate (0.1 mole) is added to 250 ml. of hydrobromic acid and the mixture is heated at reflux for 6 hours. The mixture is diluted with water and the resulting solid precipitate is separated by filtration to give 6,7-dihydro-5-methyl-1oxo-7,8,10-trihydroxy-1H,5H-benzo[ij]quinolizine-2-carboxylic acid.

EXAMPLE 26

This example illustrates the preparation of compounds of formula I wherein $R^2$ is acetamido.

10-amino-6,7-dihydro-5-methyl-1,7-dioxo-1H,5H-benzo[ij]quinolizine-2-carboxylic acid (0.02 mole) and acetic anhydride (50 ml.) are stirred and heated on a steam bath for 3 hours. After cooling, the solid precipitate is separated by filtration to give 10-acetamido-6,7-dihydro-5-methyl-1,7-dioxo-1H,5H-benzo[ij]quinolizine-2carboxylic acid. This product is reduced using sodium borohydride to provide 10-acetamido-6,7-dihydro-7-hydroxy-5-methyl-1-oxo-1H,5H-benzo[ij]quinolizine-2-carboxylic acid.

EXAMPLE 27

This example illustrates the preparation of compounds of formula I wherein $R^2$ is formamido.

A mixture of 25 ml. of formic acid and 0.2 mole 10-amino-6,7-dihydro-7-hydroxy-5-methyl-1-oxo-1H,5H-benzo-[ij]-quinolizine-2-carboxylic acid is heated at reflux for 2 hours. The solution is poured into water and the product separated by filtration is 6,7-dihydro-10-formamido-7-hydroxy-5-methyl-1-oxo-1H,5H-benzo-[ij]-quinolizine-2carboxylic acid.

What is claimed is:

1. A method for inhibiting the growth of microorganisms which comprises applying to said microorganisms an effective growth-inhibiting amount of a compound of the formula

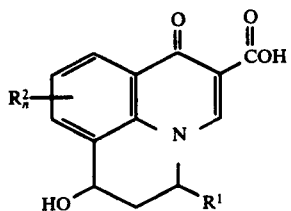

wherein $R^1$ is hydrogen, methyl or ethyl; $R^2$ is methyl, ethyl, halogen, hydroxy, nitro, amino, acetamido or formamido; $n$ is zero, one or two, and when $n$ is two, $R^2$ may be methylenedioxy or ethylenedioxy bonded to adjacent carbon atoms; and when $R^2$ is ethyl, methoxy, nitro, amino, acetamido or formamido, and $n$ is two, each $R^2$ must be different; or a lower alkyl ester or pharmaceutically acceptable salt derivative thereof.

2. The method according to claim 1 wherein the compound is contained in a conventional pharmaceutical carrier.